Figure 1:
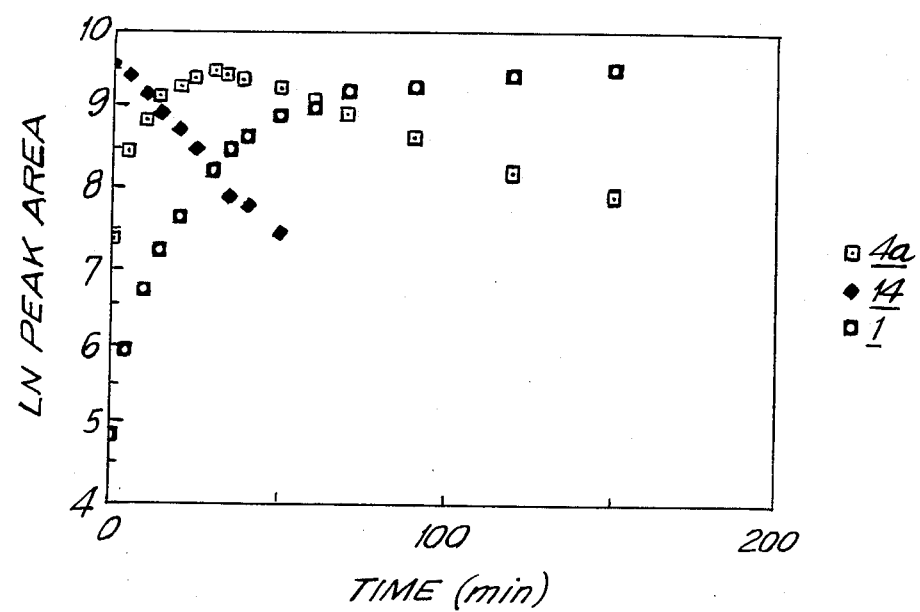

United States Patent [19]

Stella et al.

[11] Patent Number: 4,980,343
[45] Date of Patent: Dec. 25, 1990

[54] AMINOOXODIHYDROISOIN-DOLOQUINAZOLINE CARCINOSTATIC AGENTS

[75] Inventors: Valentino Stella; Laman A. Al-Razzak, both of Lawrence, Kans.; Hans-Joachim Kabbe, Leverkusen, Fed. Rep. of Germany

[73] Assignee: Bayer Aktiengesellschaft, Leverkusen, Fed. Rep. of Germany

[21] Appl. No.: 369,437

[22] Filed: Jun. 20, 1989

Related U.S. Application Data

[63] Continuation-in-part of Ser. No. 263,581, Oct. 27, 1988, abandoned.

[51] Int. Cl.$^5$ .................... A61K 31/505; C0D 487/04
[52] U.S. Cl. ........................ 514/18; 514/19; 514/267; 530/331; 544/246
[58] Field of Search .............. 544/246; 530/331; 514/18, 19, 257

[56] References Cited

U.S. PATENT DOCUMENTS

| | | | |
|---|---|---|---|
| 4,388,305 | 6/1983 | Trouet et al. | 530/331 X |
| 4,639,456 | 1/1987 | Trouet et al. | 514/283 |
| 4,732,970 | 3/1988 | Fields et al. | 530/323 |
| 4,757,072 | 7/1988 | Kabbe et al. | 514/257 |

Primary Examiner—Diana Rivers
Attorney, Agent, or Firm—Sprung Horn Kramer & Woods

[57] ABSTRACT

Therapeutic compositions comprising the new derivatives of aminooxodihydroisoindolo-quinazoline of the formula

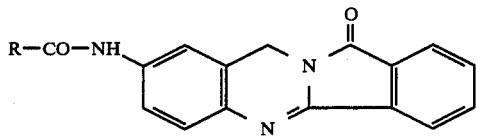

are useful in inhibiting the growth of colon and rectal tumors.

5 Claims, 1 Drawing Sheet

AMINOOXODIHYDROISOINDOLOQUINAZOLINE CARCINOSTATIC AGENTS

This application is a continuation-in-part of U.S. application Ser. No. 263,581, filed Oct. 27, 1988, which is now abandoned.

The heterocyclic amine 1 (aminooxodihydroisoindoloquinazoline; in short: AQ) has been found to exhibit excellent tumor inhibiting properties in the model of colon 38 carcinoma in the mouse [U.S. Pat. No. 4,757,072]. This model is representative for the action against cancer of the colon and rectum in humans.

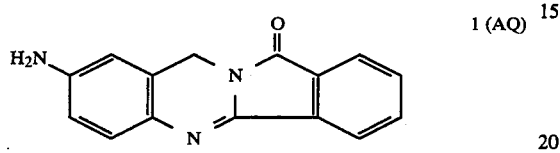

1 is, however, only poorly soluble in water and water containing solvents. Thus the formulation of concentrated aqueous solutions for parenteral application is severely hindered.

Since the oral application of 1 might result in erratic amounts of absorbed drug it is very desirable to obtain formulations for parenteral application.

It has now been found that 1 can be converted into derivatives being sufficiently soluble in water and water containing solvents as they are suitable for parenteral application of the active principle 1.

The new derivatives of 1 are reconverted into 1 by the action of enzymes like peptidases which are present in plasma and other organs.

It has now been found, that amides 2

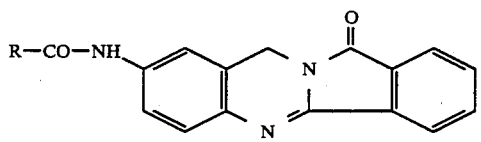

in which R—CO—NH— denotes the radical of an amino acid, of a dipeptide or of a tripeptide show enhanced solubility in water. The compounds 2 are very stable in aqueous buffer solutions (pH 4–10) but are rapidly cleaved back to AQ (1) by the action of peptidases that are present in human plasma.

Preferred radicals R—CO—NH— are those of the natural occurring amino acids and of dipeptides and tripeptides derived from these amino acids.

The compounds according to the general formula 2 are new. If R is the radical of an amino acid containing an additional amino or carboxyl group the compounds 2 may be used as neutral compounds or as salts with pharmacologically acceptable acids or bases, respectively.

The radicals R—CO—NH— are for example: N-glycyl-, N-alanyl-, N-leucyl-, N-isoleucyl-, N-valyl-, N-seryl-, N-threonyl-, N-phenylalanyl-, N-tyrosyl-, N-tryptophanyl-, N-prolyl-, N-lysyl-, N-arginyl-, N-histidyl-, N-aspartyl-, N-glutaminyl-, N-cysteinyl-, N-methionyl-, N-glycyl-alanyl-, N-dialanyl-, N-alanyl-glycyl-, N-alanyl-phenylalanyl-, N-trialanyl-, N-alanyl-lysyl-, N-lysyl-alanyl-, N-glycyl-lysyl, N-glycyl-prolyl, N-glycyl-alanyl-lysyl-, N-trialanyl-, N-lysyl-alanyl-phenylalanyl-or other peptide derivatives.

This result is surprising, since in the related case of ciprofloxacin (A) the derivatization of A with alanine leads to compound B which is stable in the presence of peptidases or human plasma, respectively. B is not cleaved back to A.

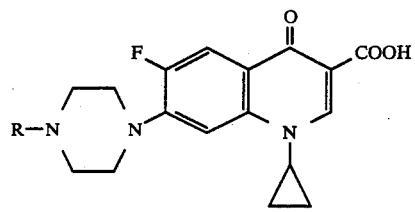

A: R = H

B: R = CH$_3$—CH—CO—
         |
         NH$_2$

As it can be seen from results below, A is effective against E. coli Neumann in vitro and in vivo. In contrast to that B is only poorly effective in both experiments: If B would be cleaved back to A by the action of plasma enzymes or chemically, B should be as effective as A in the animal model.

In vitro:

The minimal inhibitory concentrations (MICs) were determined by agar dilution method. Series of agar plates with Iso-Sensitest agar (Oxoid) were prepared which contained the test substances at twofold increasing concentrations. The agar plates were inoculated by using a multipoint inoculator (Denley). For this purpose, overnight cultures of the bacterial test strains were diluted appropriately so that each inoculation point contained approx. $10^4$ cells. The inoculated agar plates were incubated at 37° C. and bacterial growth was read after 20 hours.

|            | A     | B   |
|------------|-------|-----|
| (MIC, mg/l): | 0.015 | 0.5 |

In vivo:

To measure the therapeutic efficacy, 10 female CF1 mice each group were infected by intraperitoneal injection of $3 \times 10^7$ cells of E. coli Neumann. For treatment, one single dose of drug was given intravenously 30 min. after the infection. The survival of the animals was recorded daily until the sixth day after infection:

| mg/kg i.v. | A  | B |
|------------|----|---|
| 0.06       | 2  | 0 |
| 0.25       | 8  | 1 |
| 0.5        | 10 | 1 |

EXAMPLES

Example 1

Synthesis of N-l-alanyl-AQ-monohydrochloride (4)

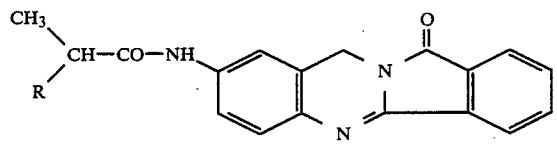

3: R = —NH—CO—O—C(CH$_3$)$_3$ [—NH-t-boc]

4: R = —NH$_2$.HCl    4a: R = NH$_2$

5: R = —NH$_2$.2CF$_3$COOH (a) Synthesis of t-boc-l-alanine derivative of AQ (3)

A solution of 500 mg of 1 in 300 ml of anhydrous methylene chloride (Aldrich, anhydrous, 99+%) was allowed to stir overnight under nitrogen atmosphere with N-t-boc-l-alanine (Sigma, St. Louis, MO., 840 mg, 4.4 mmol), N,N'-dicyclohexyl carbodiimide (DCC, Sigma, 830 mg, 4 mmol) and 30 mg of dimethyl amino pyridine (DMAP). The reaction was monitored with TLC [silica gel, methylene chloride:acetone (10:1); 1 and 3 had R$_f$ values of 0.22 and 0.12 respectively] until completion (20 hrs). The resulting white precipitate of dicyclohexylurea (DCU) was removed by filtration. The solvent was removed in vacuo and the yellow residue was purified on silica gel column (silica gel 70–230 mesh, methylene chloride:acetone, 10:1): The AQ reaction mixture was dissolved in 50:50 acetone:methylene chloride mixture, and the resulting solution was adsorbed on silica gel by adding the silica gel to the solution and evaporating the solvent in vacuo, the resulting reaction mixture adsorbed on silica gel was applied to the top of the silica gel column. Compound 3 was obtained in 92% yield as a yellow amorphous powder, m.p. 216°–218° C. Mass spectrum for 3 displayed a molecular ion of m/e 408, elemental analysis calculated C, 65.70; N, 13.32; H, 5,75, found C, 65,56; N, 13.12; H, 6.00.

(b) Synthesis of the hydrochloride salt of N-l-alanine derivative of AQ (4)

Method 1: A solution of 3 (100 mg, 0.24 mmol) in 10 ml anhydrous methylene chloride with 5 ml trifluoroacetic acid was allowed to stir at room temperature. The reaction was monitored by HPLC to completion (1 hour). The solvent was evaporated in vacuo and analyzed using HPLC. HPLC analysis showed the product di-trifluoroacetic acid salt of N-l-alanyl AQ (5) to be 95% pure. The di-trifluoroacetic acid salt 5 was converted to the monohydrochloric acid salt (4) by dissolving 100 mg of the di-trifluoroacetic acid salt 5 in 20 ml of water and adjusting the pH of the resulting solution to pH 9.0 with 0.1N NaOH solution. The resulting N-l-alanyl-AQ free base 4a was extracted with methylene chloride (25 ml×3) until the HPLC analysis of the aqueous layer showed complete extraction of 4a. The solvent was evaporated in vacuo, 50 mg of the resulting compound (0.156 mmol) in 10 ml water was mixed with 1.5 ml of 0.1N HCl (0.15 mmol) solution. After complete dissolution (2 min), the solution was filtered through a millipore microfilter and freeze dried. The purity of the resulting monohydrochloric acid salt (4) was determined with HPLC and found to be 99%. $^1$H and $^{13}$C NMR data for 1 are presented in Tables 1 and 2, while data for 4 are given in Tables 3 and 4 respectively.

M.P. of 4 was 260° C. (decomposed).

Analysis: C$_{18}$H$_{16}$N$_4$O$_2$. HCl . 2H$_2$O MW 392.85, calc.: C55.03 H 5.30 N14.26;

found: 55.10 5.56 14.00,

Two moles of water were confirmed by Karl-Fischer-titration.

There are other procedures to convert compound 3 to 4 (e.g. using formic acid for the deprotection of N-t-boc group followed by ion exchange chromatography), however the above method is found to be an easy route and the product obtained was very pure.

Method 2: A solution of 3 (100 mg, 0.24 mmol) in 10 ml anhydrous methylene chloride and 5 mmol of iodotrimethylsilane (Aldrich) was allowed to stir under nitrogen until complete deprotection of the t-boc group. The solvent and excess iodotrimethylsilane was removed in vacuo and the resulting salt (di-HI) was converted to the monohydrochloric acid salt, 4, using the same procedure mentioned above in method 1.

HPLC Assay of 1 and 4: The following HPLC conditions were used for the analysis of 1 & 4.

| | |
|---|---|
| Column | (15 × 4.6 i.d.); 5 μM MOS Hypersil (C$_8$) |
| Mobile phase | 1.5 part CH$_3$CN: 8.5 part 0.05M phosphate buffer at pH 2.5; 5 mmol of tetrabutyl ammonium hydrogen sulfate (TBAS) |
| detection | UV 275 nm, Kratos Model 7125 |
| Flow rate | 2 ml/min |
| Chart speed | 0.5 cm/min |
| Range | 0.04 aufs |
| Injection volume | 20 μl |
| Retention volume | 1    10 ml |
| | 4    5.36 ml |

TABLE 1

$^1$HNMR data for AQ 1, in MDSO-d$_6$

| Chemical shift | integration | multiplicity | assignment | J(Hz) |
|---|---|---|---|---|
| 2.516 | | | DMSO-d$_6$ | |
| 4.820 | 2H | singlet | C$_3$ | |
| 5.567 | 2H | doublet | NH$_2$ | 2.4 |
| 6.477 | 1H | doublet | C$_2$ | 2.4 |
| 6.512 | 1H | doublet of doublet | C$_{11}$ | 6.6, 2.4 |
| 7.130 | 1H | doublet | C$_{10}$ | 8.4 |
| 7.68–7.803 | 2H | doublet of doublet | C$_6$, C$_7$ | 0.9, 2.7, 7.2 |
| 7.855–7.88 | 1H | doublet | C$_5$ | 7.2 |
| 7.943–7.97 | 1H | doublet | C$_8$ | 7.2 |

TABLE 2

$^{13}$C NMR data for AQ 1, in DMSO-d$_6$

| Chemical shift (δ ppm) | Assignment |
|---|---|
| 38.92–40.365 | C$_3$, solvent |
| 111.63 | C$_2$ |
| 113.12 | C$_{11}$ |
| 121.25 | C$_5$ |
| 122.636 | C$_8$ |
| 128.85 | C$_{10}$ |
| 129.78 | C$_{8'}$ |
| 131.32 | C$_6$ |
| 132.85 | C$_7$ |
| 134.24 | C$_{4'}$ |
| 148.70 | C$_1$ |
| 155.18 | C=N |
| 165.95 | C=O |

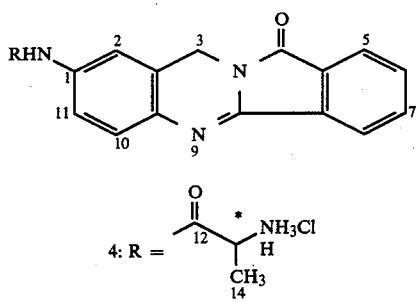

4: R = [structure with C12, NH3Cl, CH3 at C14]

TABLE 3

$^1$H NMR data for N-1-alanyl-AQ-monohydrochloric acid salt 4 in $D_2O$

| Chemical shift | integration | multiplicity | assignment | J(Hz) |
|---|---|---|---|---|
| 1.45 | 3H | doublet | (14)$CH_3$ | 7.8 |
| 3.92 | 1H | singlet | (13)CH | |
| 3.94 | 2H | broad singlet | (3)$CH_2$ | |
| 6.31–6.28 | 1H | doublet | $C_2$ | 8.7 |
| 6.42–6.39 | 1H | doublet | $C_{11}$ | 8.4 |
| 6.576 | 1H | singlet | $C_{10}$ | |
| 7.11–7.08 | 1H | doublet | $C_7$ | 7.8 |
| 7.21–7.26 | 1H | triplet | $C_6$ | 7.8 |
| 7.28–7.3 | 1H | doublet | $C_5$ | 5.4 |
| 7.35–7.325 | 1H | doublet | $C_8$ | 7.2 |

TABLE 4

$^{13}$C NMR data for N-1-alanyl-AQ-monohydrochloric acid salt (4), in $D_2O$

| Chemical shift (δ ppm) | Assignment |
|---|---|
| 17.99 | $C_{14}$ |
| 40.84 | $C_3$ |
| 50.799 | $C_{13}$ |
| 118.83 | $C_2$ |
| 120.54 | $C_{11}$ |
| 121.97 | $C_5$ |
| 122.77 | $C_8$ |
| 124.096 | $C_{10}$ |
| 127.635 | $C_{2'}$ |
| 129.54 | $C_{8'}$ |
| 132.91 | $C_6$ |
| 133.91 | $C_7$ |
| 134.85 | $C_1$ |
| 149.00 | C=N |
| 168.83 | (4)C=O |
| 169.31 | C=O(amid) |

Example 2

Synthesis of the N-l-leucine derivative of AQ (6)

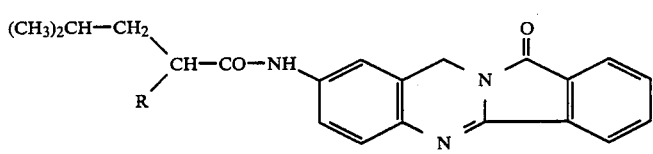

6: R = —$NH_2$·HCl

7: R = —NH—CO—O—C($CH_3$)$_3$

8: R = —$NH_2$·2$CF_3COOH$

9: R = —$NH_2$

Synthesis of N-t-boc-l-leucine derivative of AQ (7):

A solution of 500 mg of 1 in 330 ml of anhydrous methylene chloride (Aldrich, anhydrous, 99+%) was allowed to stir overnight under nitrogen atmosphere with N-t-boc-l-leucine monohydrate (Sigma, St. Louis, MO., 1000 mg, 4.0 mmol), N,N'-dicyclohexyl carbodiimide (DCC, Sigma, 830 mg, 4 mmol) and 30 mg of dimethyl amino pyridine (DMAP). The reaction was monitored with TLC [silica gel, methylene chloride:acetone (10:2); 1 and 7 had $R_f$ values of 0.24 and 0.40, respectively] until no further changes were observed in the TLC analysis (48 hours). The resulting white precipitate of dicyclohexylurea (DCU) was removed by filtration. The solvent was removed in vacuo and the yellow residue was purified on silica gel column (silica gel 70–230 mesh, methylene chloride:acetone, 10:1). (The reaction mixture was dissolved in 50:50 acetone:methylene chloride mixture, and the resulting solution was adsorbed on silica gel by adding the silica gel to the solution and evaporating the solvent in vacuo, the resulting reaction mixture adsorbed on silica gel was applied to the top of the silica gel column. Compound 7 was obtained in 80% yield as a yellow amorphous powder. Mass spectrum displayed a molecular ion of 462.

Synthesis of the hydrochloride of the N-l-leucine derivative of AQ (6):

Method 1: A solution of 7 (100 mg, 0.216 mmol) in 10 ml anhydrous methylene chloride with 5 ml trifluoroacetic acid was allowed to stir at room temperature. The reaction was monitored by HPLC or by TLC [silica gel, methylene chloride:acetone (10:2); $R_f$ value for 8 0.0] to completion (1 hour). The solvent was evaporated in vacuo and analyzed using HPLC. HPLC analysis showed 8 as the di-trifluoroacetic acid salt of N-l-leucine AQ was 95% pure. The di-trifluoroacetic acid salt, 8 was converted to the monohydrochloric acid salt (6) by dissolving 100 mg of the di-trifluoroacetic 8 in 20 ml of water and adjusting the pH of the resulting solution to pH 9.0 with 0.1N NaOH solution. The resulting N-l-leucine AQ was extracted with methylene chloride (25 ml×3). The solvent was evaporated in vacuo, 70 mg of the resulting compound (0.193 mmol) in 10 ml water was mixed with 1.9 ml of 0.1N HCl (0.19 mmol). After 6 has dissolved (about 2 min) the solution was filtered through a millipore microfilter and freeze dried. The purity of the resulting monohydrochloric acid salt 6 was determined with HPLC and found to be 99%. Compound 9 displayed a molecular ion z/e of 362. Elemental analysis for 9, calculated: C, 69.59; H, 6.12; N, 15.46. Found: C, 69.46; H, 6.18; N, 15.19.

M. P. for compound 6 is 197–200° C. (decomposed). $^1$H and $^{13}$C NMR data for 6 are presented in Tables 5 and 6 respectively. Elemental analysis for 6 ($C_{21}H_{22}N_4O_2$·HCl·2$H_2O$) calculated: C, 57.94; H, 6.26; N, 12.88; found: C, 57.95; H, 6.00; N, 12.48.

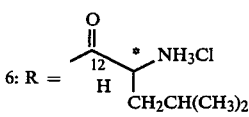

HPLC Assay of 1 and 6:

The following HPLC conditions were used for the analysis of 1 & 6:

| Column | (15 × 4.6 i.d.); 5 μM MOS Hypersil (C8) |
|---|---|
| Mobile phase | 18 part CH3CN: 82 part 0.05M phosphate buffer at pH 2.5; 5 mmol of tetrabutyl ammonium hydrogen sulfate (TBAS) |
| detection | UV 275 nm, Kratos Model 7125 |
| Flow rate | 2 ml/min |
| Chart speed | 0.5 cm/min |
| Range | 0.04 aufs |
| Injection volume | 20 μl |
| Retention volume | 1   8.0 ml |
|  | 6   12.6 ml |

TABLE 5

$^1$H NMR data for 6 in D$_2$O.

| Chemical shift | integration | multiplicity | JHz | assignment |
|---|---|---|---|---|
| 1.101 | 6H | triplet | 6.0 | (CH3)2 |
| 1.837 | 3H | multiplet |  | CH, CH2 |
| 4.069 | 1H | singlet |  | CH—NH2 |
| 4.10 | 2H | broad singlet |  | C3 |
| 6.431–6.459 | 1H | doublet | 8.4 | C2 |
| 6.610–6.638 | 1H | doublet | 8.4 | C11 |
| 6.803 | 1H | singlet |  | C10 |
| 7.216–7.239 | 1H | doublet | 6.9 | C7 |
| 7.392–7.433 | 2H | triplet | 5.7 | C5,6 |
| 7.464–7.488 | 1H | doublet | 7.2 | C8 |

TABLE 6

$^{13}$C NMR data for 6 in D$_2$O.

| Chemical shift (δ ppm) | Assignment |
|---|---|
| 22.04 | CH3 |
| 23.44 | CH3 |
| 25.19 | CH |
| 41.33 | C3 |
| 41.97 | CH2 |
| 53.56 | CH—NH2 |
| 119.30 | C2 |
| 120.96 | C11 |
| 122.03 | C5 |
| 122.69 | C8 |
| 123.98 | C10 |
| 127.85 | C2' |
| 129.50 | C8' |
| 133.00 | C6 |
| 134.81 | C7 |
| 135.33 | C4' |
| 137.38 | C1 |
| 148.87 | C=N |
| 168.71 | (4)C=O |
| 169.42 | amide C=O |

Example 3

Synthesis of the N-l-lysine dihydrochloride derivative of AQ (12)

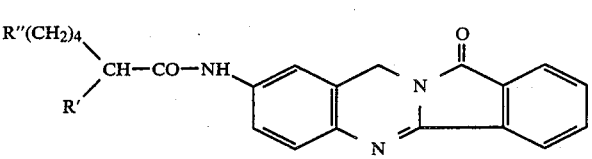

10: R', R'' = —NH2

11: R', R'' = —NH—CO—O—C(CH3)3

12: R', R'' = —NH2.HCl

13: R', R'' = —NH2.HCOOH

Synthesis of N-α,ε-di-t-boc-l-lysine derivative of AQ (11):

A solution of (500 mg, 2 mmol) of 1 in 300 ml of anhydrous methylene chloride (Aldrich) was allowed to stir overnight under a nitrogen atmosphere with N-α,ε-di-t-boc-l-lysine (1384 mg, 4.0 mmol); 1,3-dicyclohexyl carbodiimide (DCC, 830 mg, 4 mmol) and 30 mg of dimethyl amino pyridine (DMAP). The reaction was monitored by TLC (silica gel, methylene chloride::acetone 5:1) until completion. The resulting precipitate of dicyclohexylurea (DCU) was removed by filtration. The solvent was removed in vacuo and the yellow residue was purified twice on silica gel column (silica gel 70–230 mesh, methylene chloride:acetone, 5:1). Compound 11 was obtained in 90% yield as a yellow amorphous powder m.p. 170°–173° C.

Synthesis of the N-l-lysine dihydrochloride derivative of AQ (12):

A solution of 11 (100 mg, 0.173 mmol) in 5 ml of formic acid was allowed to stir at room temperature. The reaction was monitored by HPLC until completion (3 hours). HPLC analysis showed 13 as the di-formic acid salt was 90% pure, therefore, it was crystallized from ethyl acetate. The diformic acid salt was converted to the dihydrochloric acid salt by passing it through a prepared ion exchange column (QAE-Sephadex, A-25, Pharmacia Inc. N.J.). The resulting solution was freeze dried to give a yellow fluffy material with water solubility greater than 20 mg/ml. 12: m.p. 195° C. (dec.). Elemental analysis for 12 (C$_{21}$H$_{23}$N$_5$H$_2$.2HCl.3.5H$_2$O), calculated: C, 49.13; H, 6.28; N, 13.64. Found: C, 48.98; H, 6.58; N, 13.99. $^1$H and $^{13}$C NMR for 12 are presented in Tables 7 and 8 respectively.

HPLC Assay of 1 and 12:

The following HPLC conditions were used for the analysis of 1 & 12

| Column | (15 × 4.6 i.d.); 5 μM MOS Hypersil (C8) |
|---|---|
| Mobile phase | 2.0 part CH3CN: 8.0 part 0.05M phosphate buffer at pH 2.5; 0.1 mmol of tetrabutyl ammonium hydrogen sulfate (TBAS) |
| detection | UV 275 nm, Kratos Model 7125 |
| Flow rate | 1 ml/min |
| Chart speed | 0.5 cm/min |
| Range | 0.04 aufs |
| Injection volume | 20 μl |
| Retention volume | 1   10.0 ml |
|  | 12   4.0 ml |

TABLE 7

¹H NMR data for 13 in DMSO-d₆

| Chemical shift | integration | multiplicity | assignment |
|---|---|---|---|
| 1.383 | 9H | singlet | $\epsilon C(CH_3)_3$ |
| 1.407 | 9H | singlet | $(15)C(CH_3)_3$ |
| 1.6 | 2H | broad quartet | $\gamma CH_2$ |
| 1.8 | 2H | broad quartet | $\delta CH_2$ |
| 2.107 | 1H | singlet | $\epsilon NH$ |
| 3.327 | 2H | broad singlet | $\beta CH_2$ |
| 3.351 | 2H | broad singlet | $\epsilon CH_2$ |
| 4.05 | 1H | quartet | (13)CH |
| 4.953 | 2H | singlet | $C_3$ |
| 4.782 | 1H | singlet | $\alpha NH$ |
| 7.04–7.07 | 1H | doublet | $C_2$ |
| 7.38–7.41 | 1H | doublet | $C_{11}$ |
| 7.58–7.59 | 1H | doublet | $C_{10}$ |
| 7.78–7.79 | 1H | doublet | $C_7$ |
| 7.83–7.84 | 1H | doublet | $C_5$ |
| 7.91–7.94 | 1H | doublet | $C_6$ |
| 8.02–8.04 | 1H | doublet | $C_8$ |

TABLE 8

¹³C NMR data for 13 in DMSO-d₆

| Chemical shift (δ ppm) | assignment |
|---|---|
| 23.14 | $\gamma CH_2$ |
| 28.27 | $\beta CH_2$ |
| 32.86 | $\delta CH_2$ |
| 40.28 | $C_3$ |
| 41.59 | $\epsilon CH_2$ |
| 55.6 | (13)CH |
| 119.52 | $C_2$ |
| 120.94 | $C_{11}$ |
| 123.24 | $C_5$ |
| 122.78 | $C_8$ |
| 124.17 | $C_{10}$ |
| 128.92 | $C_6$ |
| 133.62 | $C_7$ |
| 135.4 | $C_{4'}$ |
| 137.55 | $C_1$ |
| 138.89 | C=N |
| 164.86 | (4)C=O |
| 168.38 | (12)C=O |
| 169.97 | HC=O |
| 170.03 | HC=O |

Example 4

Synthesis of N-t-boc-L-Gly-Ala-derivative of AQ (15)

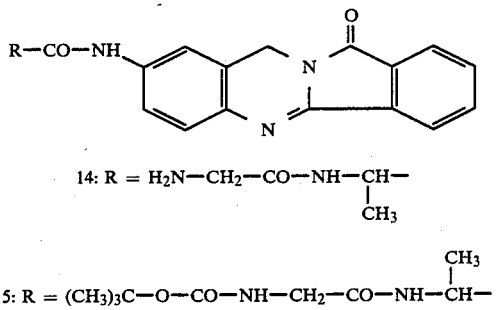

14: R = H₂N—CH₂—CO—NH—CH—
                              |
                              CH₃

15: R = (CH₃)₃C—O—CO—NH—CH₂—CO—NH—CH—
                                           |
                                           CH₃

A solution of 100 mg (0.31 mmol) of the l-alanyl-derivative of AQ in 100 ml of anhydrous methylene chloride (Aldrich, anhydrous, 99+%) was allowed to stir overnight under nitrogen atmosphere with N-t-boc-glycin (Sigma, St. Louis, MO., 160 mg, 0.62 mmol); N,N'-dicyclohexyl carbodiimide (DCC, Sigma, 130 mg, 0.62 mmol) and 4.0 mg of dimethyl amino pyridine (DMAP). The reaction was monitored with TLC (silica gel, methylene chloride:acetone:methanol (8:2:0.5)) until no further changes was observed in the TLC analysis (48 hours). The resulting white precipitate of dicyclohexylurea (DCU) was removed by filtration. The solvent was removed in vacuo and the yellow residue was purified on silica gel column (silica gel 70–230 mesh, methylene chloride:acetone:methanol 8:2:0.5). [Note: the reaction mixture was dissolved in acetone, methylene chloride, and methanol mixture until clear solution was obtained, the resulting solution was adsorbed on silica gel by adding the silica gel to the solution and evaporating the solvent in vacuo and applied it to the top of the silica gel column]. The solvent was evaporated and the product was recrystallized from methylene chloride ethyl acetate mixture. Compound 14 was obtained in 40% yield as a yellow powder. The other major byproduct was characterized to be tri- and tetrapeptide derivative of 1. Mass spectrum of 14 displayed a molecular ion m/z of 477. ¹H NMR and ¹³C NMR data for 14 are presented in Table 9 and 10 respectively.

Synthesis of L-Gly-Ala-derivative of AQ (14):

A solution of 15 (20 mg, 0.04 mmol) and 5 ml trifluoroacetic acid in 10 ml anhydrous methylene chloride was allowed to stir at room temperature. The reaction was monitored by HPLC and TLC (silica gel 70–230 mesh, methylene chloride:acetone:methanol 8:2:0.5) to completion ≈30 min. The solvent was evaporated in vacuo and the residue was analyzed using HPLC. HPLC analysis showed 14 as the di-trifluoroacetic acid salt was 98% pure. Compound 14 was purified by adjusting the pH of the aqueous solution of difluoroacetic acid salt of 14 to pH 8.0 with 0.1N sodium hydroxide solution and extraction with methylene chloride. The solvent was removed under N₂. Compound 14 displayed a molecular ion m/z of 378 in chemical ionization mass spectroscopy (molecular ion+1).

Stability studies of 14 in human plasma and 0.05M phosphate buffer pH 7.4 at 37.0° C.:

The hydrolysis of 14 in human plasma was studied. A solution containing 2.0 mg of 14 in 200 μl of water was mixed with 2 ml of human plasma (sodium citrate was used as anticoagulant). The resulting mixture was placed in water bath at 37.0° C. Samples were withdrawn at appropriate time intervals and proteins were precipitated with 250 μl of acetonitrile, vortexed for 30 sec, the centrifuged for 15 min at 2200 rpm. A 100 μl sample of the supernatent was mixed with 250 μl of H₂O and the resulting solution was analyzed by HPLC. Compound 14 was hydrolyzed to 4a with a half life of 14.0±1.0 min and subsequently to 1. Compound 4a was hydrolyzed to 1 as shown in FIG. 1 with a half life of ≈20 min, consistent with our earlier finding (Note: similar result was obtained when the final concentration of 14 in plasma was 0.1 mg/ml). The chemical hydrolysis of 14 (5.5×10⁻⁵M) in 0.05M phosphate buffer pH 7.4 and ionic strength of 0.15M (NaCl) at 37.0° C. was studied. Samples were withdrawn and analyzed at appropriate time intervals. HPLC analysis showed hydrolysis of 14 to 1 with a half life of 2.5 days.

TABLE 9

¹H NMR data for 15 in DMSO.

| Chemical shift | integration | multiplicity | JHz | assignment |
|---|---|---|---|---|
| 1.343–1.364 | 1H | doublet | 6.3 | $CH_3$ |
| 1.414 | 9H | singlet | — | $C(\underline{CH}_3)_3$ |
| 3.638–3.655 | 2H | doublet | 5.1 | $CH_2(gly)$ |
| 4.037–4.063 | 1H | quartet | 7.8 | $\underline{CH}-CH_3$ |
| 4.457–4.506 | 1H | triplet | 7.5 | $\underline{H}N(gly\text{-}t\text{-}boc)$ |
| 4.894 | 2H | singlet | — | $C_3$ |

TABLE 9-continued

<sup>1</sup>H NMR data for 15 in DMSO.

| Chemical shift | integration | multiplicity | JHz | assignment |
|---|---|---|---|---|
| 7.061 | 1H | triplet | 5.1 | NH(gly-ala) |
| 7.334–7.365 | 1H | doublet | 9.3 | $C_{10}$ |
| 7.559–7.578 | 2H | doublet | 5.7 | $C_{2,11}$ |
| 7.769 | 2H | quartet, doublet | 7.8 | $C_{7,6}$ |
| 7.853–7.880 | 1H | doublet | 8.1 | $C_8$ |
| 7.956–7.982 | 1H | doublet | 7.8 | $C_5$ |
| 10.156 | 1H | singlet | | HN(1) |

TABLE 10

<sup>13</sup>C NMR data for 14 in $D_2O$.

| Chemical shift (δ ppm) | Assignment |
|---|---|
| 18.267 | $CH_3$ |
| 28.24 | $(CH_3)_3$ |
| 49.087 | CH—$CH_3$ |
| 59.796 | $CH_2$(GLY) |
| 78.197 | $C(CH_3)_3$ |
| 117.711 | $C_2$ |
| 119.045 | $C_{11}$ |
| 121.797 | $C_5$ |
| 122.424 | $C_8$ |
| 122.811 | $C_{10}$ |
| 127.912 | $C_{2'}$ |
| 130.049 | $C_{8'}$ |
| 132.212 | $C_6$ |
| 133.160 | $C_7$ |
| 134.122 | $C_{4'}$ |
| 135.711 | $C_9$ |
| 138.181 | $C_1$ |
| 147.582 | C=N |
| 155.968 | amide C=O (t-boc) |
| 166.170 | (4) C=O |
| 169.241 | amide C=O (batracyn-Ala) |
| 171.284 | amide C=O (Ala-Gly) |

Example 5

Solubility of acylated derivatives 2

Whereas 1 is nearly insoluble in water the hydrochloric acid salt 4 exhibits a solubility of more than 25 mg per ml water.

Aqueous solutions of the hydrochloric acid salts 6 and 12 are obtainable with concentrations of more than 25 mg compound per ml.

Example 6

Stability studies of compounds 4, 6 and 12 in aqueous buffered solutions:

The hydrolysis of 4, 6 or 12 in aqueous buffered solutions at various pH and at an ionic strength of 0.15 (NaCl) were measured by analyzing aliquots at appropriate intervals using HPLC. In the HPLC analysis both the disappearance of 4, 6 or 12 and the appearance of 1 were monitored. Rate constants were calculated from the first-order plots of the disappearance of 4, 6 or 12 versus time. The results obtained from these studies are shown in table 11.

TABLE 11

Stability of 4, 6 or 12 in aqueous buffered solutions ($\mu$ = 0.15).

| Solvent, temp. | compound | pH | initial conc. mg/ml | $k_{obs}$ $hr^{-1}$ | $t_{\frac{1}{2}}$ hr |
|---|---|---|---|---|---|
| Acetate (0.05M), 25° C. | 4 | 5.0 | 0.024 | $1.60 \times 10^{-3}$ | 427.0 |
| | 6 | 5.0 | 0.018 | $1.1 \times 10^{-3}$ | 624.0* |
| | 12 | 5.0 | 0.024 | $1.15 \times 10^{-3}$ | 600.0* |

TABLE 11-continued

Stability of 4, 6 or 12 in aqueous buffered solutions ($\mu$ = 0.15).

| Solvent, temp. | compound | pH | initial conc. mg/ml | $k_{obs}$ $hr^{-1}$ | $t_{\frac{1}{2}}$ hr |
|---|---|---|---|---|---|
| Water, 25° C. | 4 | 4.5 | 10.0 | | >480* |
| | 4 | 5.9 | 0.1 | | >480* |
| | 6 | 4.31 | 10.0 | $1.46 \times 10^{-4}$ | 4746* |
| | 6 | 5.46 | 0.1 | $6.10 \times 10^{-4}$ | 1128* |
| | 12 | 4.54 | 10.0 | $2.67 \times 10^{-4}$ | 2592* |
| | 12 | 6.1 | 0.1 | $7.80 \times 10^{-4}$ | 888* |
| Phosphate (0.05M), 25° C. | 4 | 7.4 | 0.02 | | >200* |
| | 6 | 7.4 | 0.02 | $4.11 \times 10^{-3}$ | 168.6 |
| | 12 | 7.4 | 0.02 | $2.58 \times 10^{-3}$ | 268.8 |
| Phosphate (0.05M), 37° C. | 4 | 7.4 | 0.02 | $4.40 \times 10^{-3}$ | 158.0 |
| | 6 | 7.4 | 0.02 | $8.60 \times 10^{-3}$ | 80.6 |
| | 12 | 7.4 | 0.02 | $1.03 \times 10^{-2}$ | 67.2 |

*estimated values

Example 7

Stability studies of 4, 6 and 12 in human and mice plasma

A solution of approximately 2.0 mg of 4, 6 or 12 in 100 μl of water was added to 2 ml of either human or mice plasma. The resulting solution was placed in water bath at 37° C. Samples were withdrawn at appropriate time intervals and proteins were precipitated with 250 μl of acetonitrile, vortexed for 30 sec., then centrifuged for 10 min at 2200 rpm. HPLC analysis of the supernatant showed quantitative hydrolysis of 4, 6 or 12 to 1. Apparent first-order rate constants were obtained by plotting the disappearance the derivatives 4, 6 or 12 versus time on semilogarithmic plot and the results are shown in table 12.

TABLE 12

Stability of the derivatives of AQ 4, 6 and 12 in human and mice plasma at 37° C.

| compound | species | anticoagulant | kobs (min)$^{-1}$ | $t_{\frac{1}{2}}$ (min) | r |
|---|---|---|---|---|---|
| 4 | human 1 | citrate | $2.5 \times 10^{-2}$ | 27.6 | 0.995 |
| 4 | human 2 | citrate | $2.2 \times 10^{-2}$ | 30.7 | 0.985 |
| 4 | mice | heparin | $3.3 \times 10^{-2}$ | 21.3 | 0.992 |
| 6 | human | citrate | $5.7 \times 10^{-3}$ | 121.5 | 0.977 |
| 6 | mice | heparin | $1.85 \times 10^{-2}$ | 37.4 | 0.998 |
| 12 | human | citrate | $5.0 \times 10^{-3}$ | 138.6 | 0.991 |
| 12 | mice | heparin | $4.8 \times 10^{-3}$ | 146.0 | 0.994 |

We claim:

1. An aminooxodihydroisoindolo-quinazoline of the general formula

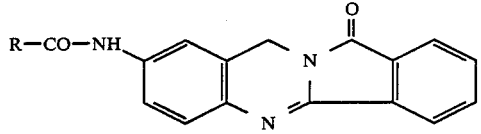

in which the radical R—CO—NH— represents the radical of an amino acid, a dipeptide or a tripeptide or a physiologically acceptable salt thereof.

2. An aminooxodihydroisoindolo-quinazoline according to claim 1 in which the radical of an amino acid is derived from a naturally occurring amino acid.

3. An aminooxodihydroisoindolo-quinazoline according to claim 1 in which the radical R—CO—NH— represents N-glycyl-, N-alanyl-, N-leucyl-, N-isoleucyl-, N-valyl-, N-seryl-, N-threonyl-, N-phenylalanyl-, N- tyrosyl-, N-tryptophanyl-, N-prolyl-, N-lysyl-, N-arginyl-, N-histidyl-, N-aspartyl-, N-glutaminyl-, N-cysteinyl-, N-methionyl-, N-glycyl-alanyl-, N-dialanyl-, N-alanyl-glycyl-, N-alanyl-phenylalanyl-, N-trialanyl-, N-alanyl-lysyl-, N-lysyl-alanyl-, N-glycyl-lysyl-, N-glycyl-prolyl, N-glycyl-alanyl-lysyl-, N-trialanyl-, N-lysyl-alanyl-phenylalanyl-or other peptide derivatives.

4. A method of combating or inhibiting carcinoma of the colon and/or rectum comprising administering to a patient having a carcinoma of the colon and/or rectum a therapeutically effective amount for combating or inhibiting carcinoma of the colon and/or rectum of an aminooxodihydroisoindolo-quinazoline according to claim 1.

5. A therapeutic composition in parenteral solution form useful in the treatment of carcinoma of the colon and/or rectum comprising water or a water-containing solvent and a therapeutically effective amount for inhibiting carcinoma of the colon and/or rectum of an aminooxodihydroisoindolo-quinazoline according to claim 1.

* * * * *